(12) United States Patent
Creaven

(10) Patent No.: US 8,048,098 B2
(45) Date of Patent: Nov. 1, 2011

(54) LANCING DEVICE FOR ONE SKIN PUNCTURE

(75) Inventor: John P. Creaven, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 160 days.

(21) Appl. No.: 11/988,713

(22) PCT Filed: Jul. 13, 2006

(86) PCT No.: PCT/US2006/027213
§ 371 (c)(1),
(2), (4) Date: Jan. 11, 2008

(87) PCT Pub. No.: WO2007/011645
PCT Pub. Date: Jan. 25, 2007

(65) Prior Publication Data
US 2009/0082798 A1    Mar. 26, 2009

Related U.S. Application Data

(60) Provisional application No. 60/699,117, filed on Jul. 14, 2005.

(51) Int. Cl.
*A61B 17/14* (2006.01)
(52) U.S. Cl. ........................................... 606/182
(58) Field of Classification Search .................. 606/181, 606/182, 167, 183; 604/136, 137, 138, 139; 600/573, 583
See application file for complete search history.

(56) References Cited

U.S. PATENT DOCUMENTS

| | | | |
|---|---|---|---|
| 3,797,488 A | | 3/1974 | Hurschman et al. ........ 128/218 F |
| 4,203,446 A | * | 5/1980 | Hofert et al. ................... 606/182 |
| 4,442,836 A | | 4/1984 | Meinecke et al. ............ 128/314 |
| 4,449,529 A | | 5/1984 | Burns et al. .................... 128/314 |
| 4,469,110 A | | 9/1984 | Slama ............................ 128/770 |
| 4,517,978 A | | 5/1985 | Levin et al. .................... 128/314 |
| 4,535,769 A | * | 8/1985 | Burns ........................... 606/182 |

(Continued)

FOREIGN PATENT DOCUMENTS

DE    459 483    5/1928

(Continued)

OTHER PUBLICATIONS

Written Opinion corresponding to International Patent Application No. PCT/US2006/027213, European Patent Office, dated Nov. 10, 2006, 6 pages.

(Continued)

*Primary Examiner* — S. Thomas Hughes
*Assistant Examiner* — Jonathan W Miles
(74) *Attorney, Agent, or Firm* — Nixon Peabody LLP

(57) ABSTRACT

A lancing device comprises a main housing, a movable housing, and a damping ring. The main housing forming an inner aperture that encloses a portion of a lancet assembly. The lancet assembly has a lancet body, a lancet-plunger housing, and a lance. The lancet assembly is adapted to move between a resting position, a cocking position, and a puncture position. The movable housing is adjacent to the main housing. The moveable housing is adapted to move from a resting position to a cocking position. The moveable housing is adapted to connect to the lancet assembly. The damping ring is adapted to engage the lancet assembly as the lancet assembly moves from the puncture position back towards the resting position to reduce movement of the lancet assembly back towards the puncture position.

18 Claims, 4 Drawing Sheets

U.S. PATENT DOCUMENTS

| | | | | |
|---|---|---|---|---|
| 4,553,541 A | 11/1985 | Burns | | 128/314 |
| 4,627,445 A | 12/1986 | Garcia et al. | | 128/770 |
| 4,637,403 A | 1/1987 | Garcia et al. | | 128/770 |
| 4,735,203 A | 4/1988 | Ryder et al. | | 128/314 |
| D297,459 S | 8/1988 | Heiland et al. | | D24/28 |
| 4,787,398 A | 11/1988 | Garcia et al. | | 128/770 |
| RE32,922 E | 5/1989 | Levin et al. | | 128/314 |
| 4,924,879 A | 5/1990 | O'Brien | | 128/770 |
| 4,976,724 A | 12/1990 | Nieto et al. | | 606/182 |
| 4,990,154 A | 2/1991 | Brown et al. | | 606/192 |
| 5,074,872 A | 12/1991 | Brown et al. | | 606/182 |
| D332,490 S | 1/1993 | Brown et al. | | D24/130 |
| 5,196,025 A | 3/1993 | Ranalletta et al. | | 606/182 |
| 5,231,993 A | 8/1993 | Haber et al. | | 128/770 |
| 5,267,963 A | 12/1993 | Bachynsky | | 604/134 |
| 5,279,294 A | 1/1994 | Anderson et al. | | 128/633 |
| 5,304,193 A | 4/1994 | Zhadanov | | 606/182 |
| 5,318,583 A | 6/1994 | Rabenau et al. | | 606/182 |
| 5,320,607 A | 6/1994 | Ishibashi | | 604/115 |
| 5,350,392 A | 9/1994 | Purcell et al. | | 606/182 |
| 5,527,334 A | 6/1996 | Kanner et al. | | 606/182 |
| 5,575,777 A | 11/1996 | Cover et al. | | 604/198 |
| 5,628,764 A | 5/1997 | Schraga | | 606/182 |
| D393,716 S | 4/1998 | Brenneman et al. | | D24/147 |
| D393,717 S | 4/1998 | Brenneman et al. | | D24/147 |
| 5,741,288 A | 4/1998 | Rife | | 606/181 |
| 5,797,942 A | 8/1998 | Schraga | | 606/182 |
| 5,868,772 A | 2/1999 | LeVaughn et al. | | 606/181 |
| 5,916,230 A | 6/1999 | Brenneman et al. | | 606/172 |
| 5,951,492 A | 9/1999 | Douglas et al. | | 600/583 |
| 5,951,493 A | 9/1999 | Douglas et al. | | 600/583 |
| 5,954,738 A * | 9/1999 | LeVaughn et al. | | 606/181 |
| 6,022,366 A | 2/2000 | Schraga | | 606/181 |
| 6,045,567 A | 4/2000 | Taylor et al. | | 606/181 |
| 6,048,352 A | 4/2000 | Douglas et al. | | 606/181 |
| 6,050,977 A | 4/2000 | Adams | | 604/195 |
| 6,090,078 A | 7/2000 | Erskine | | 604/198 |
| 6,090,124 A | 7/2000 | Weekes | | 606/182 |
| 6,093,156 A | 7/2000 | Cunningham et al. | | 600/573 |
| 6,093,468 A * | 7/2000 | Toms et al. | | 428/67 |
| 6,099,484 A | 8/2000 | Douglas et al. | | 600/583 |
| 6,152,942 A | 11/2000 | Brenneman et al. | | 606/181 |
| 6,156,051 A | 12/2000 | Schraga | | 606/181 |
| 6,168,606 B1 | 1/2001 | Levin et al. | | 606/181 |
| 6,197,040 B1 | 3/2001 | LeVaughn et al. | | 606/182 |
| 6,210,421 B1 | 4/2001 | Böcker et al. | | 606/182 |
| 6,231,531 B1 | 5/2001 | Lum et al. | | 601/46 |
| 6,283,982 B1 | 9/2001 | LeVaughn et al. | | 606/172 |
| 6,306,152 B1 | 10/2001 | Verdonk et al. | | 606/182 |
| 6,322,574 B1 | 11/2001 | Lloyd et al. | | 606/181 |
| 6,364,889 B1 | 4/2002 | Kheiri et al. | | 606/181 |
| 6,409,740 B1 | 6/2002 | Kuhr et al. | | 606/182 |
| 6,419,661 B1 | 7/2002 | Kuhr et al. | | 604/207 |
| 6,432,120 B1 | 8/2002 | Teo | | 606/182 |
| 6,451,040 B1 | 9/2002 | Purcell | | 606/181 |
| 6,514,270 B1 | 2/2003 | Schraga | | 606/182 |
| 6,537,292 B1 | 3/2003 | Lee | | 606/182 |
| 6,561,989 B2 | 5/2003 | Whitson | | 600/573 |
| 6,602,268 B2 | 8/2003 | Kuhr et al. | | 606/181 |
| 6,607,543 B2 | 8/2003 | Purcell et al. | | 606/181 |
| 6,749,618 B2 * | 6/2004 | Levaughn et al. | | 606/182 |
| 6,752,817 B2 | 6/2004 | Flora et al. | | 606/181 |
| 6,837,858 B2 | 1/2005 | Cunningham et al. | | 600/573 |
| 7,144,404 B2 | 12/2006 | Whitson et al. | | 606/181 |
| 7,175,642 B2 * | 2/2007 | Briggs et al. | | 606/181 |
| 7,238,192 B2 | 7/2007 | List et al. | | 606/182 |
| 7,291,117 B2 * | 11/2007 | Boecker et al. | | 600/583 |
| 7,303,573 B2 | 12/2007 | D'Agostino | | 606/181 |
| 2002/0022789 A1 | 2/2002 | Perez et al. | | 600/573 |
| 2003/0171696 A1 | 9/2003 | Dosmann | | 600/583 |
| 2003/0171699 A1 | 9/2003 | Brenneman | | 600/584 |
| 2003/0216767 A1 | 11/2003 | List et al. | | 606/181 |
| 2004/0049219 A1 * | 3/2004 | Briggs et al. | | 606/181 |
| 2004/0059256 A1 | 3/2004 | Perez | | 600/583 |
| 2004/0248312 A1 | 12/2004 | Vreeke et al. | | 436/95 |
| 2005/0085840 A1 | 4/2005 | Yi et al. | | 606/182 |

FOREIGN PATENT DOCUMENTS

| | | |
|---|---|---|
| EP | 0 115 388 A1 | 8/1984 |
| EP | 0 204 892 A2 | 12/1986 |
| EP | 0 894 471 A2 | 2/1999 |
| EP | 0 898 936 A2 | 3/1999 |
| EP | 0 958 783 A1 | 11/1999 |
| EP | 1 541 088 | 6/2005 |
| EP | 1 625 825 | 2/2006 |
| WO | WO 02/100278 A1 | 12/2002 |
| WO | WO 2004/103178 A1 | 12/2004 |
| WO | WO 2005/001418 A2 | 1/2005 |
| WO | WO 2006/031535 A2 | 4/2005 |
| WO | WO 2005/046477 | 5/2005 |
| WO | WO 2005/077275 A1 | 8/2005 |

OTHER PUBLICATIONS

International Search Report corresponding to International Patent Application No. PCT/US2006/027213, European Patent Office, dated Nov. 10, 2006, 3 pages.

* cited by examiner

LANCING DEVICE FOR ONE SKIN PUNCTURE

CROSS-REFERENCE TO RELATED APPLICATIONS

This application claims priority to Application No. 60/699,117 filed on Jul. 14, 2005, which is incorporated by reference in its entirety.

FIELD OF THE INVENTION

The present invention relates generally to lancing devices and, more particularly, to a single-puncture lancing mechanism for a lancing device.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. The whole blood sample may then be used to determine, for example, the glucose concentration of an individual. Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination.

The whole blood sample is often obtained by piercing the skin of a test subject. In addition to the pain and discomfort inherent with such a puncture, existing lancing devices may cause increased pain to many individuals by failing to properly dampen the lancet after initially piercing the skin. This may result in multiple punctures to the individual's skin, increasing the discomfort to the user. Alternatively, excessive damping may reduce the lancet's force and adversely affect the puncture depth, causing insufficient sample size and the need to lance again.

Additionally, the cost, complexity, effectiveness, and design of lancing devices are important to individual users. Thus, it would be desirable to have a lancing device and method that address these issues.

SUMMARY OF THE INVENTION

According to one embodiment of the present invention, a lancing device comprises a main housing, a movable housing, and a damping ring. The main housing forms an inner aperture that encloses a portion of a lancet assembly. The lancet assembly has a lancet body, a lancet-plunger housing, and a lance. The lancet assembly is adapted to move between a resting position, a cocking position, and a puncture position. The movable housing is adjacent to the main housing. The moveable housing is adapted to move from a resting position to a cocking position. The moveable housing is adapted to connect to the lancet assembly. The damping ring is adapted to engage the lancet assembly as the lancet assembly moves from the puncture position back towards the resting position to reduce movement of the lancet assembly back towards the puncture position.

According to another embodiment of the present invention, a lancet assembly adapted to move between a resting position, a cocking position, and a puncture position, comprises a lancet body, a lancet-plunger housing, a lance, a spring, and a damping ring. The lancet body is adapted to move within a lancing device. The lance is connected to the lancet-plunger housing and is adapted to puncture the skin of a user. The spring is adapted to connect the lancet-plunger housing to the lancet body. The damping ring is adapted to engage the lancet-plunger housing as the lancet-plunger housing moves from the puncture position back towards the resting position to reduce movement of the lancet-plunger housing back towards the puncture position.

According to a further embodiment of the present invention, a lancing device comprises a main housing, a moveable housing, a first spring, a second spring, and a damping ring. The main housing forms an inner aperture that encloses a portion of a lancet assembly. The lancet assembly has a lancet body, a lancet-plunger housing, and a lance. The lancet assembly is adapted to move between a resting position, a cocking position, and a puncture position. The moveable housing is adjacent the main housing. The moveable housing is adapted to move from a resting position to a cocking position. The moveable housing is adapted to connect to the lancet assembly. The first spring is adapted to connect to the main housing and the lancet body. The first spring is generally wrapped around a shaft portion of the lancet assembly. The first spring is compressed as the moveable housing is moved from the resting position to the cocking position. The first spring returns to a resting position as the moveable housing returns to the resting position. The second spring is adapted to connect the lancet body and the lancet-plunger housing. The second spring extends as the lancet assembly moves from the cocking position to the puncture position. The second spring returns to a resting position as the lancet-plunger housing moves from the puncture position back towards the resting position. The damping ring is adapted to engage the lancet assembly as the lancet assembly moves from the puncture position back towards the resting position to reduce the movement of the lancet assembly back towards the puncture position.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 1b is a bottom exploded view of the lancing device of FIG. 1a.

DESCRIPTION OF ILLUSTRATED EMBODIMENTS

The present invention is directed to a lancet-release mechanism for incorporation into a stand-alone lancing device or into a lancing device that is incorporated into a meter or similar testing device. The lancing device is adapted to receive a lancet for use in drawing a body fluid from a test subject. The body fluid generally contains at least one analyte that may then be examined to determine its concentration in the body fluid sample.

Lancing devices and lancets may be used to produce a blood or body fluid sample from a test subject. This sample may then be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin $A_{1C}$, fructose, lactate, or bilirubin.

Figure 1A:
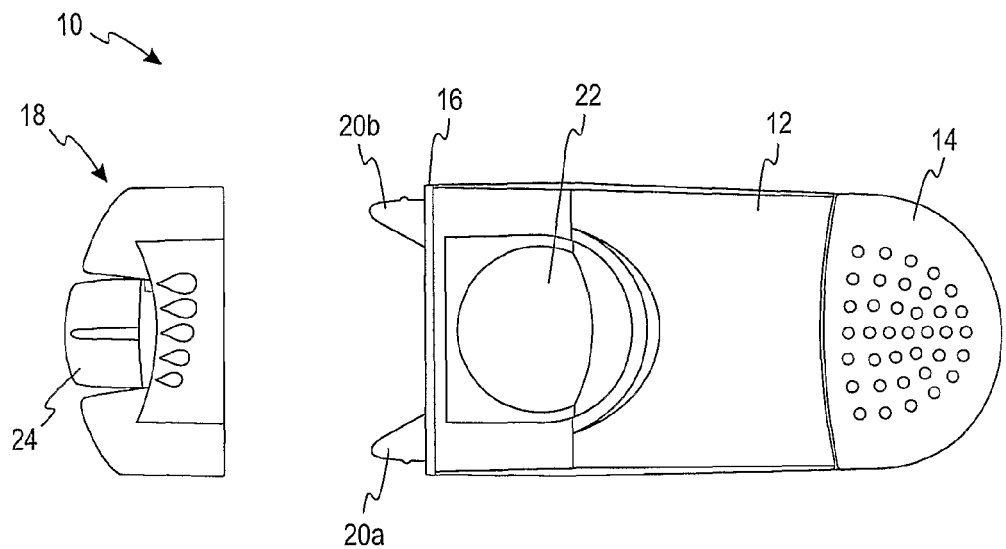
FIG. 1a is a top exploded view of a lancing device, according to one embodiment of the present invention.
Figure 1B:
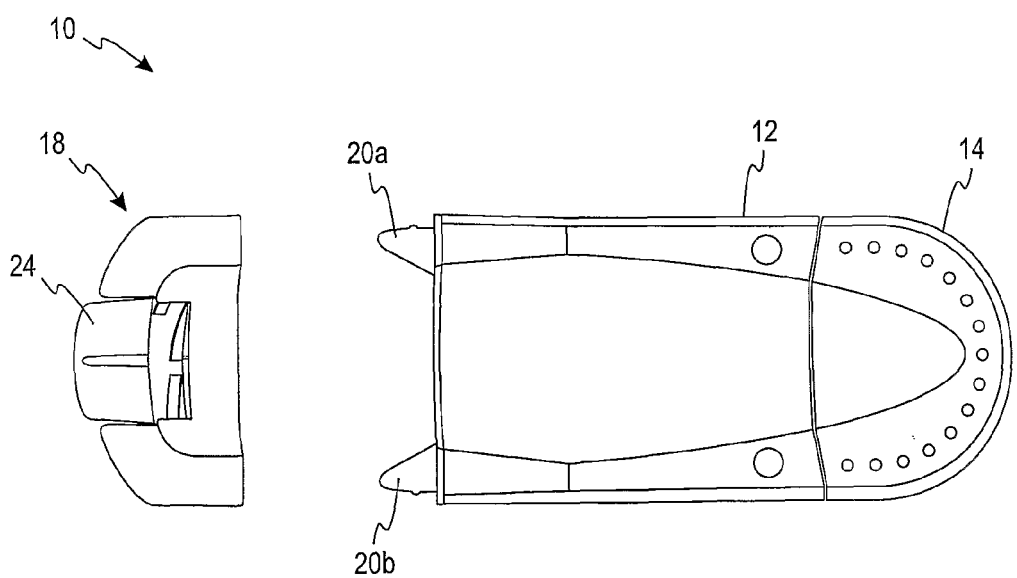
Figure 2:
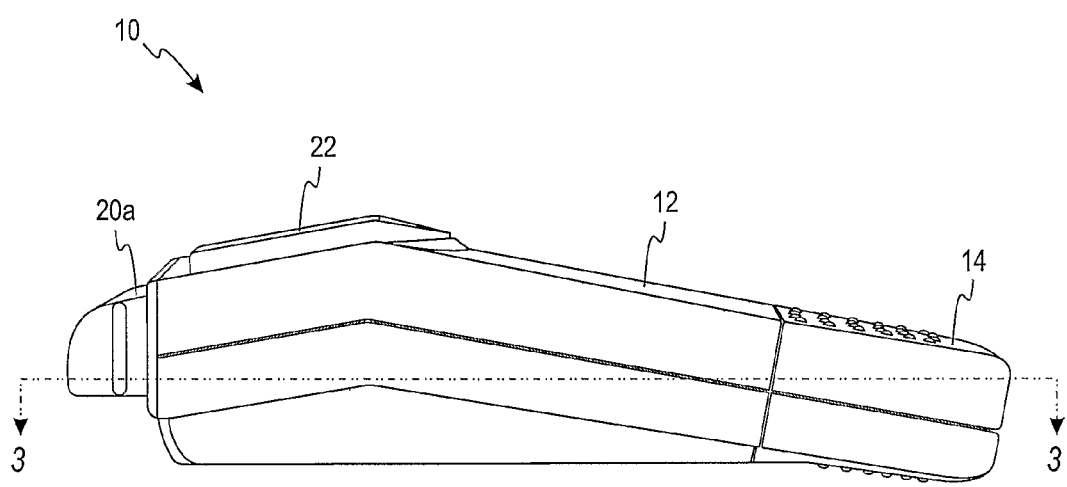
FIG. 2 is a side view of the lancing device of FIGS. 1a-b.

Turning now to the drawings and initially to FIGS. 1-2, a lancing device 10 for obtaining a fluid sample from a test subject is illustrated, according to one embodiment of the present invention. The lancing device 10 has a main housing 12 and a movable housing 14 that is movable relative to the main housing 12. An endcap support 16 is connected to the main housing 12 on the lancing end of the lancing device 10. An endcap 18 may be removably attached to the endcap support 16. When attached, the endcap 18 is retained on the endcap support 16 by a pair of support arms 20a-b integrally formed with the endcap support 16.

Figure 3:
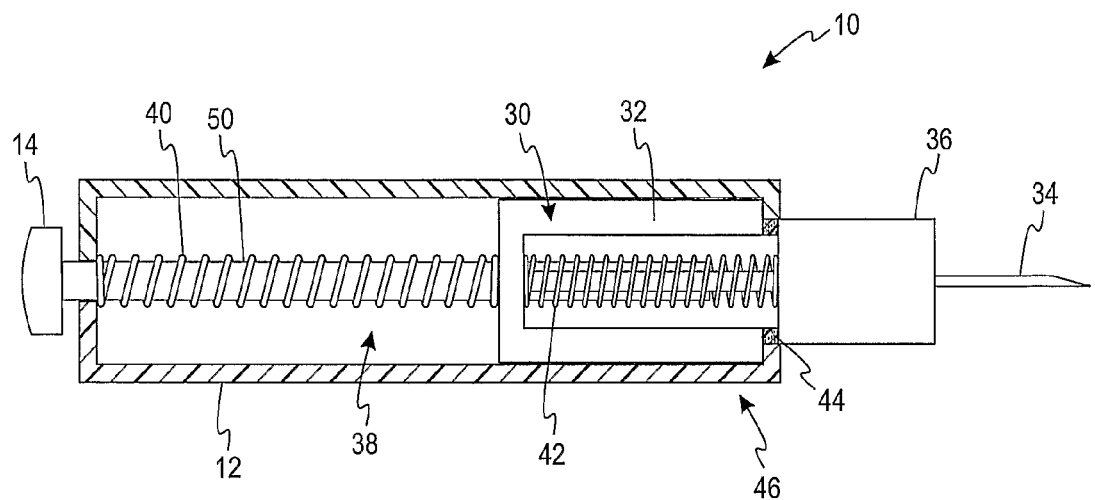
FIG. 3 is a partial, cross-sectional, top view of the lancing device of FIG. 2 in a resting position.
Figure 4:
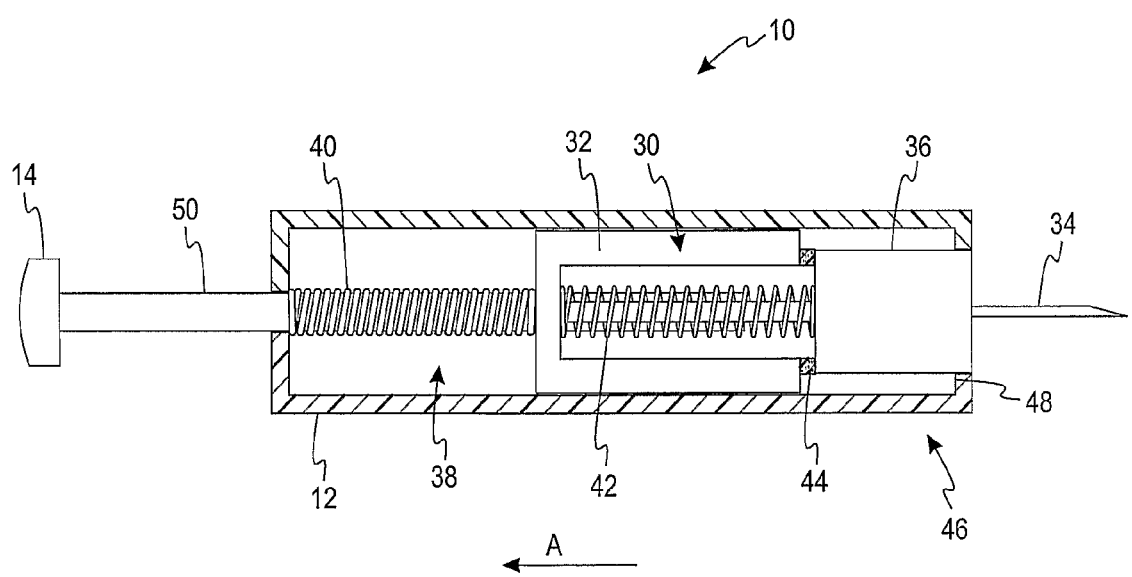
FIG. 4 is a partial, cross-sectional, top view of the lancing device of FIG. 2 in a cocking position.
Figure 5:
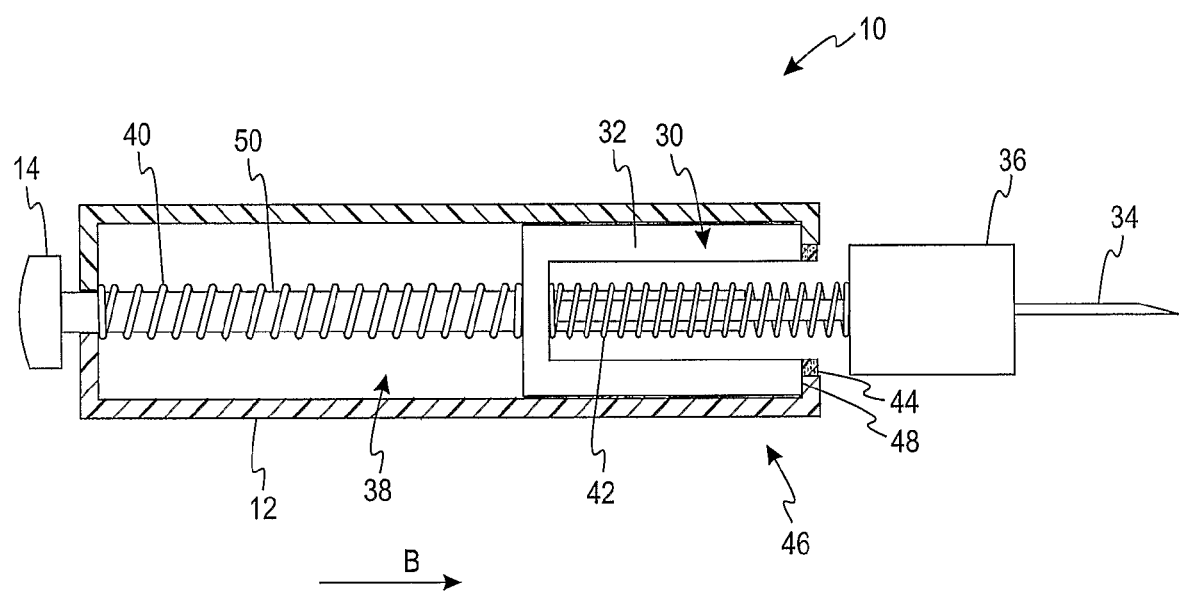
FIG. 5 is a partial, cross-sectional, top view of the lancing device of FIG. 2 in a puncture position.

To use the lancing device 10, the movable housing 14 is pulled away from the main housing 12 to move a lancet assembly 30 (as best illustrated in FIGS. 3-5) to a cocked position, and then a pushbutton 22 is pushed to actuate the lancet assembly 30 so that the sharp tip of a lancet is forced through an aperture (not shown) in the endcap 18. The lancing device 10 may be provided with a number of different endcaps 18, each having a different size, to facilitate the formation of skin punctures of various depths. Alternatively, the endcap 18 may include an adjustable dial 24 for allowing punctures of different depths to be performed utilizing a single endcap 18.

Turning now to FIG. 3, a cross-sectional view of a portion of the lancing device 10 is illustrated (with the endcap 18 and endcap support 16 not shown) in a resting position. A lancet assembly 30 having a lancet body 32, a lance 34, and a lancet-plunger housing 36 is received within an internal cylindrical aperture 38 formed within an interior of the main housing 12. The lancet body 32 and the lancet-plunger housing 36 are adapted to slide within the main housing 12. The lancet assembly 30 additionally has a shaft portion 50 adapted to connect the lancet assembly 30 to the moveable housing 14. The lancet assembly 30 further has a first spring 40 generally wrapped around the shaft portion 50 adapted to be connected to, or secured between, the main housing 12 and the lancet body 32. The lancet assembly 30 further has a second spring 42 adapted to connect to the lancet body 32 and the lancet-plunger housing 36. The second spring 42 being under a slight amount of tension in the resting position. Lancet assembly 30 additionally comprises a damping ring 44. The damping ring 44 is adapted to be attached to the lancet body 32. The damping ring is adapted to dampen the motion of the lancet-plunger housing 36 as it moves back towards the main housing 12 after lancing the skin of a user.

As shown in FIG. 4, the moveable housing 14 is adapted to be displaced in the direction of arrow A relative to the main housing 12. As the moveable housing 14 is displaced, the first spring 40 is compressed. The displacement of the moveable housing 14 additionally displaces the lancet body 32, the plunger housing 36, the lance 34, and the damping ring 44 are all moved in the direction of arrow A, into a cocked position.

Turning now to FIG. 5, the lancing device 10 is shown after the pushbutton 22 (FIG. 1a) has been depressed to fire the lance 34 into a user's skin moving the lancet assembly into a puncture position. Depressing the pushbutton 22 allows the first spring 40 to return to a non-compressed state. As the first spring 40 returns to the non-compressed state, the lancet body 32, the plunger housing 36, the lance 34, and the damping ring 44 are all moved in the direction of arrow B. As the lancet body 32 reaches a lower end 46 of the main housing 12, an inner edge 48 of the main housing stops the travel of the lancet body 32. The plunger housing 36 and the lance 34 continue to move in the direction of arrow B, from momentum generated by the first spring 40 returning to the non-compressed state, to lance a user's skin. That is, the plunger housing 36 is spaced from the damping ring 44 when the lancet assembly 30 is in the puncture position as shown in FIG. 5. As the plunger housing 36 and the lance 34 continue to move, the second spring 42 extends to a stretched position and more tension is generated within the second spring 42. After a user's skin has been lanced by the lance 34, the second spring 42 begins to return to a non-stretched position, causing the plunger housing 36 and the lance 34 to move back towards the main housing 12.

As the plunger 36 reaches the lower end 46 of the main housing 12, the plunger 36 contacts the damping ring 44. The damping ring 44 absorbs energy from the plunger 36 generated as the second spring 42 returns to the resting position wherein the second spring 42 is under a slight amount of tension. The damping ring 44 is adapted to only absorb energy from the plunger housing 36 as the second spring 42 returns to a non-stretched position. That is, the damping ring 44 is adapted to only dampen the lancet assembly 30 as the lancet assembly 30 moves from the puncture position back towards the resting position. Allowing the damping ring 44 to absorb energy from the plunger 36 helps to inhibit or reduce motion of the plunger housing 36 back in the direction of arrow A (FIG. 4). This reduces or eliminates the possibility of re-lancing a user's skin. Preventing more than one lancing of a user's skin may reduce the pain a user experiences compared with multiple lancings. Damping the movement of the plunger housing 36, and subsequently the lance 34, only as the plunger housing 36 moves towards the main housing 12, after lancing the skin, allows the lancing device 10 to properly lance a user's skin, and helps to reduce or eliminate the pain a user experiences from multiple skin punctures.

According to one embodiment, the damping ring 44 comprises a polymeric material, such as a foam polymeric material, although other materials such as rubber, silicone, and the like may be used.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

Alternative Embodiment A

A lancing device comprising:
a main housing forming an inner aperture enclosing a portion of a lancet assembly, the lancet assembly having a lancet body, a lancet-plunger housing, and a lance, the lancet assembly being adapted to move between a resting position, a cocking position, and a puncture position;

a movable housing adjacent the main housing, being adapted to move from a resting position to a cocking position, and being adapted to connect to the lancet assembly; and a damping ring adapted to engage the lancet assembly as the lancet assembly moves from the puncture position back towards the resting position to reduce movement of the lancet assembly back towards the puncture position.

Alternative Embodiment B

The lancing device of Alternative Embodiment A, wherein the damping ring is a polymeric material.

Alternative Embodiment C

The lancing device of Alternative Embodiment B, wherein the damping ring is a polymeric foam material.

Alternative Embodiment D

The lancing device of Alternative Embodiment A, wherein the damping ring is a rubber material.

Alternative Embodiment E

The lancing device of Alternative Embodiment A, wherein the lancet assembly further has a shaft portion being adapted to connect to the moveable housing.

Alternative Embodiment F

The lancing device of Alternative Embodiment E, further comprising:
a first spring adapted to connect to the main housing and the lancet body, the first spring being generally wrapped around the shaft portion of the lancet assembly, the first spring being compressed as the moveable housing is moved from the resting position to the cocking position, the first spring returning to a resting position as the moveable housing returns to the resting position; and
a second spring adapted to connect the lancet body and the lancet-plunger housing, the second spring extending as the lancet assembly moves from the cocking position to the puncture position, the second spring returning to a resting position as the lancet-plunger housing moves from the puncture position back towards the resting position.

Alternative Embodiment G

The lancing device of Alternative Embodiment A, wherein the damping ring only damps the lancet assembly as the lancet assembly moves from the puncture position back towards the resting position.

Alternative Embodiment H

A lancet assembly adapted to move between a resting position, a cocking position, and a puncture position, the lancet assembly comprising:
a lancet body adapted to move within a lancing device;
a lancet-plunger housing;
a lance connected to the lancet-plunger housing and being adapted to puncture the skin of a user;
a spring adapted to connect the lancet-plunger housing to the lancet body; and
a damping ring adapted to engage the lancet-plunger housing as the lancet-plunger housing moves from the puncture position back towards the resting position to reduce movement of the lancet-plunger housing back towards the puncture position.

Alternative Embodiment I

The lancet assembly of Alternative Embodiment H, wherein the damping ring is a polymeric material.

Alternative Embodiment J

The lancet assembly of Alternative Embodiment I, wherein the damping ring is a polymeric foam material Alternative Embodiment K The lancet assembly of Alternative Embodiment H, wherein the damping ring is a rubber material.

Alternative Embodiment L

The lancet assembly of Alternative Embodiment H, wherein the spring further is adapted to extend as the lancet assembly moves from the cocking position to the puncture position, the spring returning to a resting position as the lancet-plunger housing moves from the puncture position back towards the resting position.

Alternative Embodiment M

The lancet assembly of Alternative Embodiment H, wherein the damping ring only damps the lancet-plunger housing as the lancet-plunger housing moves from the puncture position back towards the resting position.

Alternative Embodiment N

A lancing device comprising:
a main housing forming an inner aperture enclosing a portion of a lancet assembly, the lancet assembly having a lancet body, a lancet-plunger housing, and a lance, the lancet assembly being adapted to move between a resting position, a cocking position, and a puncture position;
a moveable housing adjacent the main housing, the moveable housing being adapted to move from a resting position to a cocking position, and being adapted to connect to the lancet assembly;
a first spring adapted to connect to the main housing and the lancet body, the first spring being generally wrapped around a shaft portion of the lancet assembly, the first spring being compressed as the moveable housing is moved from the resting position to the cocking position, the first spring returning to a resting position as the moveable housing returns to the resting position;
a second spring adapted to connect the lancet body and the lancet-plunger housing, the second spring extending as the lancet assembly moves from the cocking position to the puncture position, the second spring returning to a resting position as the lancet-plunger housing moves from the puncture position back towards the resting position; and
a damping ring adapted to engage the lancet assembly as the lancet assembly moves from the puncture position back towards the resting position to reduce movement of the lancet assembly back towards the puncture position.

Alternative Embodiment O

The lancing device of Alternative Embodiment N, wherein the damping ring is a polymeric material.

Alternative Embodiment P

The lancing device of Alternative Embodiment O, wherein the damping ring is a polymeric foam material.

Alternative Embodiment Q

The lancing device of Alternative Embodiment N, wherein the damping ring is a rubber material.

Alternative Embodiment R

The lancing device of Alternative Embodiment N, wherein the damping ring only damps the lancet assembly as the lancet assembly moves from the puncture position back towards the resting position.

The invention claimed is:

1. A lancing device comprising:
a main housing forming an inner aperture enclosing a portion of a lancet assembly, the lancet assembly having a lancet body, a lancet-plunger housing, a damping ring, and a lance, the lancet assembly being adapted to move between a resting position, a cocking position, and a puncture position; and
a moveable housing adjacent the main housing, the moveable housing being adapted to move from a resting position to a cocking position, and being adapted to connect to the lancet assembly,
wherein the damping ring is adapted to engage the lancet-plunger housing as the lancet assembly moves from the puncture position back towards the resting position to reduce movement of the lancet assembly back towards the puncture position, the damping ring being directly coupled with an end surface of the lancet body such that the lancet-plunger housing abuts the damping ring in response to the lancet assembly being in the resting position and the cocking position, the lancet-plunger housing being outside of the main housing and spaced from the damping ring when the lancet assembly is in the puncture position.

2. The lancing device of claim 1, wherein the damping ring is a polymeric material.

3. The lancing device of claim 2, wherein the damping ring is a polymeric foam material.

4. The lancing device of claim 1, wherein the damping ring is a rubber material.

5. The lancing device of claim 1, wherein the lancet assembly further has a shaft portion being adapted to connect to the moveable housing.

6. The lancing device of claim 5, further comprising:
a first spring adapted to connect to the main housing and the lancet body, the first spring being generally wrapped around the shaft portion of the lancet assembly, the first spring being compressed as the moveable housing is moved from the resting position to the cocking position, the first spring returning to a resting position as the moveable housing returns to the resting position; and
a second spring adapted to connect the lancet body and the lancet-plunger housing, the second spring extending as the lancet assembly moves from the cocking position to the puncture position, the second spring returning to a resting position as the lancet-plunger housing moves from the puncture position back towards the resting position.

7. The lancing device of claim 1, wherein the damping ring only damps the lancet assembly as the lancet assembly moves from the puncture position back towards the resting position.

8. A lancet assembly adapted to move between a resting position, a cocking position, and a puncture position, the lancet assembly comprising:
a lancet body adapted to move within a lancing device;
a lancet-plunger housing;
a lance connected to the lancet-plunger housing and being adapted to puncture the skin of a user;
a spring adapted to connect the lancet-plunger housing to the lancet body; and
a damping ring adapted to directly engage the lancet-plunger housing via an impact force as the lancet assembly moves from the puncture position back towards the resting position to reduce movement of the lancet assembly back towards the puncture position, the damping ring being directly coupled with an end surface of the lancet body such that the lancet-plunger housing abuts the damping ring in response to the lancet assembly being in the resting position and the cocking position and such that the lancet-plunger housing is spaced from the damping ring when the lancet assembly is in the puncture position,
wherein the lancet-plunger housing moves independently from the lancet body when the lancet assembly moves from the puncture position to the resting position.

9. The lancet assembly of claim 8, wherein the damping ring is a polymeric material.

10. The lancet assembly of claim 9, wherein the damping ring is a polymeric foam material.

11. The lancet assembly of claim 8, wherein the damping ring is a rubber material.

12. The lancet assembly of claim 8, wherein the spring further is adapted to extend as the lancet assembly moves from the cocking position to the puncture position, the spring returning to a resting position as the lancet assembly moves from the puncture position back towards the resting position.

13. The lancet assembly of claim 8, wherein the damping ring only damps the lancet-plunger housing as the lancet assembly moves from the puncture position back towards the resting position.

14. A lancing device comprising:
a main housing forming an inner aperture enclosing a portion of a lancet assembly, the lancet assembly having a lancet body, a lancet-plunger housing, a damping ring, and a lance, the lancet assembly being adapted to move between a resting position, a cocking position, and a puncture position;
a moveable housing adjacent the main housing, the moveable housing being adapted to move from a resting position to a cocking position, and being adapted to connect to the lancet assembly;
a first spring adapted to connect to the main housing and the lancet body, the first spring being generally wrapped around a shaft portion of the lancet assembly, the first spring being compressed as the moveable housing is moved from the resting position to the cocking position, the first spring returning to a resting position as the moveable housing returns to the resting position; and
a second spring adapted to connect the lancet body and the lancet-plunger housing, the second spring extending as the lancet assembly moves from the cocking position to the puncture position, the second spring returning to a resting position as the lancet assembly moves from the puncture position back towards the resting position, wherein the damping ring is adapted to directly engage the lancet-plunger housing via an impact force as the lancet assembly moves from the puncture position back towards the resting position to reduce movement of the lancet assembly back towards the puncture position, the damping ring being directly coupled with an end surface of the lancet body such that the lancet-plunger housing abuts the damping ring in response to the lancet assembly being in the resting position and the cocking position, and wherein the lancet-plunger housing moves independently from the lancet body when the lancet assembly moves from the puncture position to the resting position and the lancet-plunger housing is outside of the main housing and spaced from the damping ring when the lancet assembly is in the puncture position.

15. The lancing device of claim 14, wherein the damping ring is a polymeric material.

16. The lancing device of claim 15, wherein the damping ring is a polymeric foam material.

17. The lancing device of claim 14, wherein the damping ring is a rubber material.

18. The lancing device of claim 14, wherein the damping ring only damps the lancet assembly as the lancet assembly moves from the puncture position back towards the resting position.

* * * * *